(12) United States Patent
Phi-Wilson et al.

(10) Patent No.: US 6,403,378 B1
(45) Date of Patent: Jun. 11, 2002

(54) CELL VIABILITY ASSAY REAGENT

(75) Inventors: Janette T. Phi-Wilson, Los Altos Hills; Don F. Rackham; Kevin M. Sheehan, both of Palo Alto, all of CA (US)

(73) Assignee: Guava Technologies, Inc., Burlingame, CA (US)

( * ) Notice: Subject to any disclaimer, the term of this patent is extended or adjusted under 35 U.S.C. 154(b) by 0 days.

(21) Appl. No.: 09/844,789

(22) Filed: Apr. 26, 2001

(51) Int. Cl.[7] .............................................. G01N 31/00
(52) U.S. Cl. ................. 436/10; 436/8; 436/63; 436/164; 436/166; 436/172; 435/29; 252/408.1
(58) Field of Search .................... 436/8, 10, 63, 436/164, 166, 172; 435/29, 39; 252/408.1

(56) References Cited

U.S. PATENT DOCUMENTS

| | | | | |
|---|---|---|---|---|
| 3,586,859 A | * | 6/1971 | Katz et al. ................ | 250/459.1 |
| 5,047,321 A | * | 9/1991 | Loken et al. .................. | 435/34 |
| 5,057,413 A | * | 10/1991 | Terstappen et al. ........... | 435/29 |
| 5,185,450 A | * | 2/1993 | Owen .......................... | 548/193 |
| 5,314,805 A | * | 5/1994 | Haugland et al. ............. | 435/29 |
| 5,879,900 A | * | 3/1999 | Kim et al. ..................... | 356/39 |

OTHER PUBLICATIONS

Frey, Tom. Detection of Bromodeoxyuridine Incorporation by Alteration of the Flourescence Emission from Nicleic Acid Binding Dyes Using Only an Argon Ion Laser. Cytometry, vol. 17, pp. 310–318, 1994.*

* cited by examiner

*Primary Examiner*—Maureen M. Wallenhorst
(74) *Attorney, Agent, or Firm*—Flehr Hohbach Test Albritton & Herbert LLP

(57) ABSTRACT

A kit for labeling cells to determine their viability which includes a first dye for labeling non-viable cells and a second dye for labeling all cells, including non-viable cells in which the dyes are selected to have concentrations suitable for determining the viability of cells in cell suspensions having different cell viability.

2 Claims, 2 Drawing Sheets

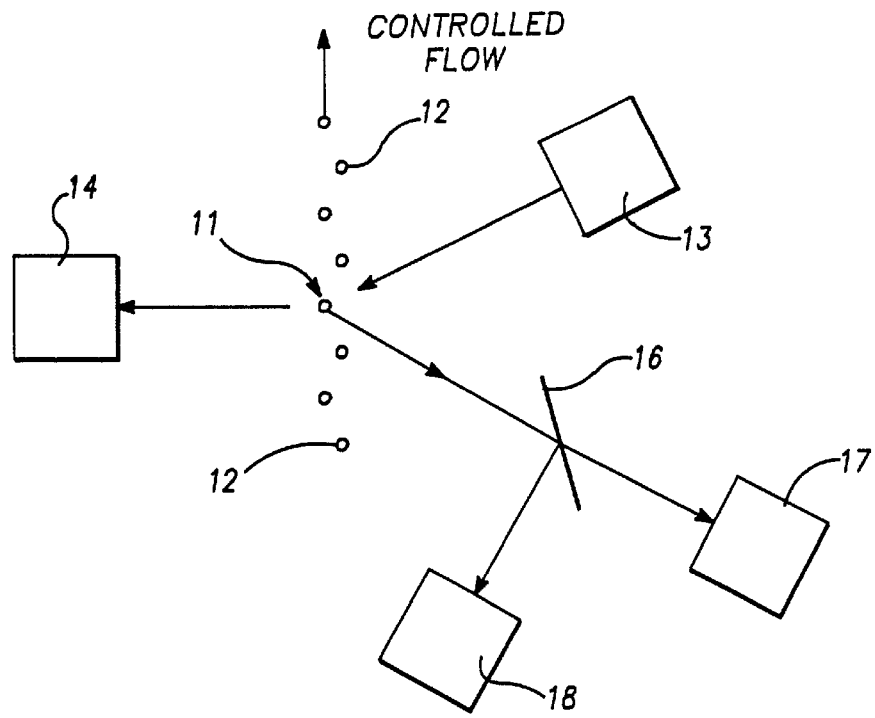
FIG.—1
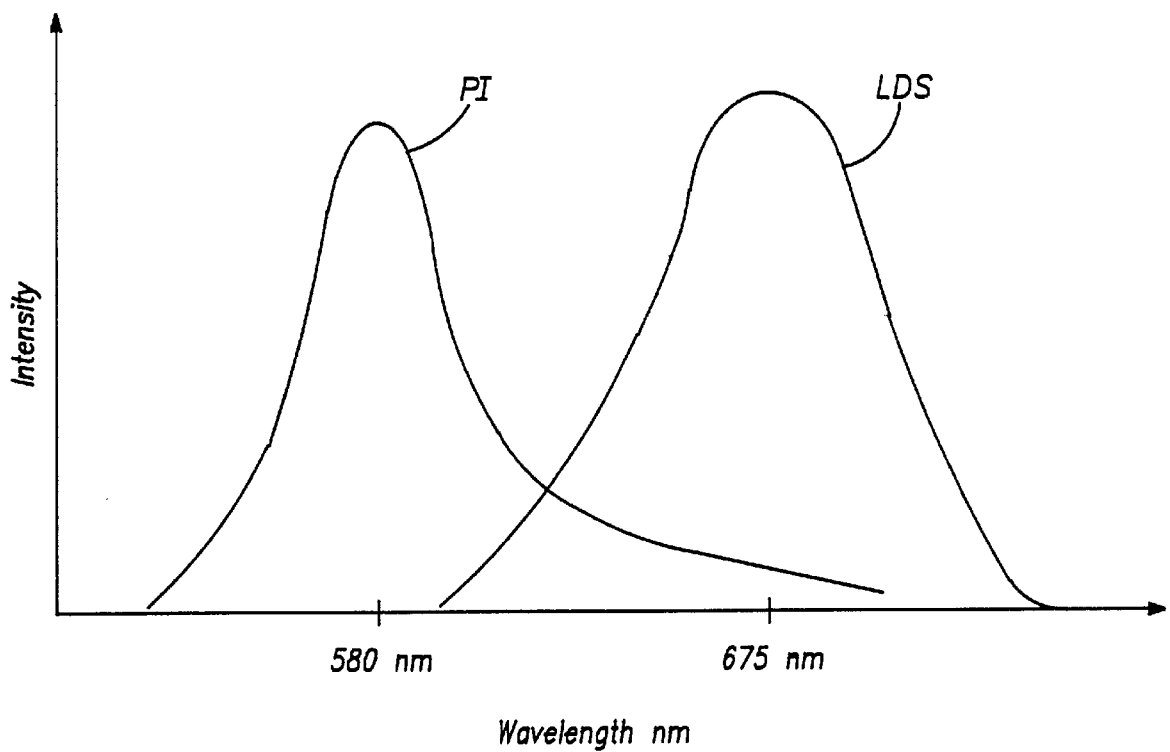
FIG.—2

CELL VIABILITY ASSAY REAGENT

BRIEF DESCRIPTION OF THE INVENTION

This invention relates generally to a cell viability assay reagent used for staining cells in a cell suspension so that all non-viable cells are stained to fluoresce at a first wavelength responsive to light at one wavelength, and all viable and non-viable cells are stained to fluoresce at a second wavelength responsive to excitation by light of a lower wavelength.

BACKGROUND OF THE INVENTION

Two dyes are generally used to stain cells in a suspension for viability analysis. One dye consists of a membrane permeant DNA dye that labels all intact cells in a suspension, whereby they emit light at one wavelength. A non-permeant DNA dye labels all dead cells.

In one method of analysis, the cells in the cell suspensions are stained and a traditional hemacytometer is used to differentiate the cells. Another analysis system utilizes dual-color fluorescence in combination with forward light scatter to determine the concentration of nucleated cells and cell viability. Cells are analyzed by providing relative movement between the sample suspension containing the cells and an excitation light beam, whereby labeled cells pass through the light beam and emit light at a wavelength characteristic of the permeant and non-permeant dye. The detection system includes filters and detectors which detect the light emitted at the two wavelengths. The cells also scatter light, whereby all particles in the sample suspension are detected. Once a cell has been detected on the permeant dye channel, the light scatter profile is evaluated to assure that the cell is of sufficient size to be an intact cell and not simply a free nucleus or other cell fragment. The second dye permeates all cells with damaged or "leaky" membranes. The dye emits fluorescent light at a different wavelength range than that of the cells stained with permeant dye. In this manner all cells are detected by detecting the light emitted by the second dye at one wavelength, and non-viable cells are detected by detecting light emitted by the permeant dye at the other wavelength. Thus, an absolute count of cells and percent viability can be obtained from the data.

To obtain reliable results for different cell concentrations, using a two-dye method it is necessary to carefully control the amount of each of the dyes used to stain or tag the cells. This is a time-consuming procedure and may lead to variability in results obtained.

SUMMARY OF THE INVENTION

The present invention is directed to a cell viability reagent which uses $C_{25}H_{30}ClN_3O_4$ obtained from Exciton Laboratories (herein LDS) and propidium iodide obtained from Sigma Chemical Company (Cat. #P4120, herein PI) to stain the cells so they emit fluorescent light having a peak value at 580 nm and 675 nm, respectively, responsive to excitation by light at 532 nm. The dye is used in a cell analysis system designed to detect the fluorescent light at the two wavelengths and provide an output indicative of cells fluorescing at one or both wavelengths.

DESCRIPTION OF THE DRAWINGS

The invention will be more clearly understood from the following description when read in connection with the accompanying drawings of which:

FIG. 1 is a schematic view of a flow cytometer useful in viability studies using the reagent of the present invention.

FIG. 2 schematically illustrates the fluorescent light amplitude as a function of wavelength for the LDS and PI dyes.

DESCRIPTION OF THE INVENTION

Figure 3:
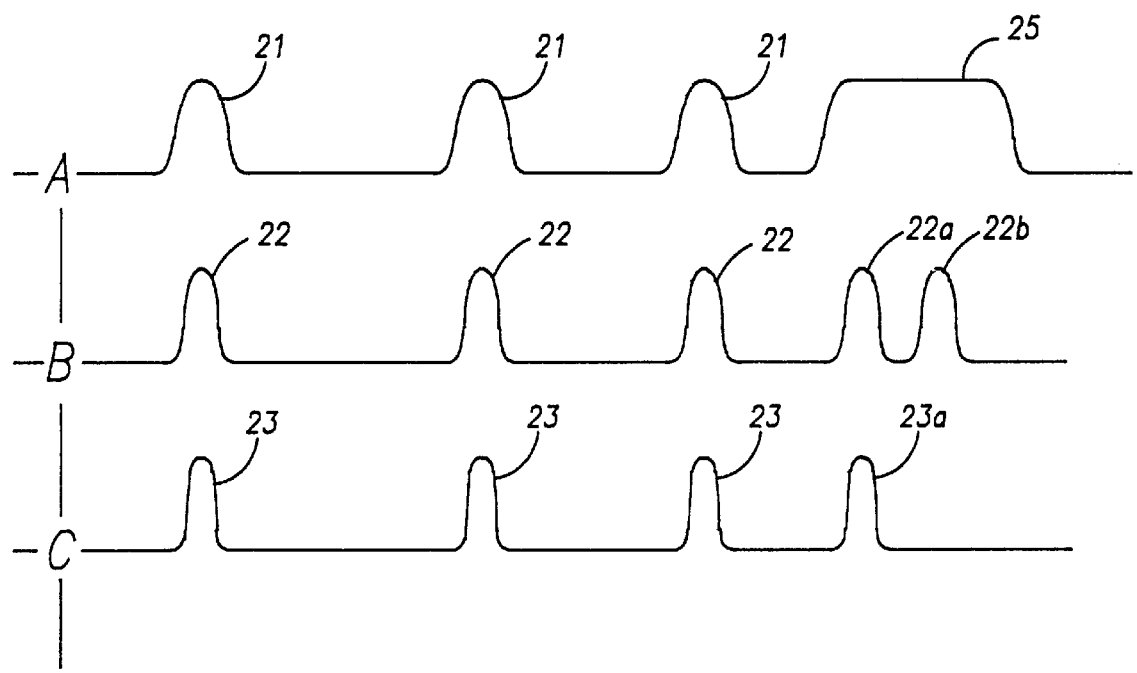
FIG. 3 illustrates the output of the photodetectors for scatter (cell presence) and for the detected fluorescent light at each of the two wavelengths, which data is analyzed to provide a measure of viability.

The particle analyzing device may be a flow cytometer employing sheath flow or a particle analyzer of the type sold by Guava Technologies, Inc. In any event, the cell suspension is caused to flow past an analyzing volume 11 with the cells 12 singulated. The particles are excited by light from a suitable light source 13 such as a diode laser. Scattered light is detected by detector 14 which is used to provide an absolute count of all particles or cells passing through the analyzing volume whether tagged with a fluorescent dye or not. Cells which have been tagged with fluorescent dyes emit light at corresponding wavelengths. The emitted light for all tagged cells is applied to a dichroic beam splitter 16. The beam splitter transmits light having wavelengths above a given wavelength to a detector assembly 17, which may include a filter, and reflects emitted light having wavelengths below the given wavelength to a detector assembly 18 which may include a filter.

FIG. 2 shows the wavelengths of the fluorescent light emitted by the LDS and PI dyes responsive to excitation light having a wavelength of 532 nm peaks at 580 nm and 675 nm, respectively, for the LDS and PI dyes. The filters in the detectors can selected to pass light in the ranges 545–610 nm and 630–725 nm, and to be able to distinguish between the emitted light at the two wavelengths.

Referring particularly to FIG. 3A, the pulses correspond to the output of the scatter detector 14, which provides one pulse 21 per particle, cell or aggregate that passes through the analyzing volume. FIG. 3B indicates the passage of all tagged cells whether viable or dead which emit fluorescent light at a first wavelength. FIG. 3C indicates non-viable cells which emit light at the second wavelength. Thus, all cells which emit light at the first wavelength are seen as pulses 22, while non-viable or dead cells, which emit light at a second wavelength are seen as pulses 23. The pulses can then be counted for a predetermined or measured time, and cell viability, cell count and cell concentration determined. In some instances cells are clustered as shown by the enlarged scatter pulse 25. Within the scatter pulse more than one cell is present. As shown in the figure, two cells are present, 22a, 22b, one of which 23a is non-viable.

It was found during cell analysis that if there was not enough LDS or PI reagent or dye, some cells were not stained and the results would therefore be inaccurate. On the other hand, when excess dye was present, the output fluorescent light pulses, FIG. 2, overlapped and the differentiation between the two wavelengths could not be consistently maintained, thereby providing inaccurate results. We discovered that by providing a reagent having the proper concentration of both the LDS and the PI dye or stain, accurate and repeatable results could be obtained for a wide range of cell concentrations.

To this end we prepared twenty reagent solutions as follows. LDS 5 µg/ml; 1 µg/ml; 0.2 µg/ml and 0 µg each with PI 10 µg/ml; 2.5 µg/ml; 0.63 µg/ml; 0.6 µg/ml and 0 µg/ml. The LDS reagent was prepared by dissolving LDS obtained from Exciton Laboratories (Catalog #LDS751) dissolved in methanol or DMSO and then diluted to the desired concentration with a PE buffer comprising phosphate-buffered saline, pH 7.4 supplemented with 5 mM EDTA (ethylenediaminetetraacetic acid). The propidium iodide was obtained from Sigma Chemical Company (Catalog #P4170) and was dissolved in phosphate-buffered saline pH 7.2 before dilution with the PE buffer to the desired concentrations for use in the above matrix.

A Jurkat cell suspension was prepared at three different viabilities in order to assess the effect on cell culture viability and staining profile for each of the twenty reagent concentration combinations. Cells were counted and viabilities determined by microscopy using Trypan blue and Acridine orange/Ethidium bromide staining solutions. Samples of each suspension having different viabilities were then stained with one of the twenty reagent solutions noted above. Cell concentration and viability were then determined with a cell analyzing system of the type discussed above. This permitted assessment of the range of reagent concentration effective to carry out assays for cell suspensions having cells with different viabilities. The results of our study showed that the concentration of LDS and PI in the reagent which provided accurate cell and viability data was in the range of 0.5–10 µg/ml for LDS and 0.16–5 µg/ml for PI, when using a 532 nm laser source and detectors designed to detect wavelengths between 545 and 610 nm for the propidium iodide and 630–775 nm for the LDS. A more preferable range of concentration for LDS was 1–5 µg/ml for LDS and 0.63–2.5 µg/ml for the PI. Thus, there has been provided a viability reagent kit which simplifies the tagging or staining of cells for the determination of cell viability.

What is claimed is:

1. A cell viability reagent for labeling cells with fluorescent stain to determine cell viability using a cytometer which excites the labeled cells with light at 532 nm and which has a two-color detecting system for detecting light having wavelengths in the 545–610 and 630–775 nanometer ranges emitted by fluorescently-labeled cells comprising a solution having a concentration of LDS in the range of 0.5–10 µg/ml and propidium iodide (PI) in the range of 0.16 5 µg/ml.

2. A cell viability reagent as in claim 1 in which the solution has a concentration in the range of 1–5 µg/ml for LDS and 0.13–2.5 µg/ml for PI.

* * * * *

UNITED STATES PATENT AND TRADEMARK OFFICE
CERTIFICATE OF CORRECTION

PATENT NO. : 6,403,378 B1
DATED : June 11, 2002
INVENTOR(S) : Janette T. Phi-Wilson et al.

It is certified that error appears in the above-identified patent and that said Letters Patent is hereby corrected as shown below:

<u>Column 4,</u>
Line 17, number "0.16 5" should read -- 0.16-5 --.
Line 20, number "0.13-2.5" should read -- 0.63-2.5 --.

Signed and Sealed this

Twenty-first Day of June, 2005

JON W. DUDAS
*Director of the United States Patent and Trademark Office*